United States Patent [19]

Aufderhaar et al.

[11] 4,436,660
[45] Mar. 13, 1984

[54] PROCESS FOR THE PRODUCTION OF 5-CYANO-AND 5-CARBOXAMIDO-5H-DIBENZ[B,F]AZEPINES

[75] Inventors: Ernst Aufderhaar, Kaiseraugst; Klemenz Sprecher, Basel; János Zergényi, Seltisberg, all of Switzerland

[73] Assignee: Ciba-Geigy Corporation, Ardsley, N.Y.

[21] Appl. No.: 378,464

[22] Filed: May 14, 1982

Related U.S. Application Data

[63] Continuation of Ser. No. 198,887, Oct. 20, 1980, abandoned.

[30] Foreign Application Priority Data

Oct. 30, 1979 [CH] Switzerland ......................... 9705/79

[51] Int. Cl.$^3$ ............................................ C07D 223/26
[52] U.S. Cl. ................................................ 260/239 D
[58] Field of Search .................................... 260/239 D

[56] References Cited

U.S. PATENT DOCUMENTS 2,762,796  9/1956  Morel et al. .................... 260/239 D

OTHER PUBLICATIONS

Z. Rappaport (Ed) "The Chem. of the Cyano Group", pp. 78, 79, 256–263, Interscience, N.Y., N.Y. (1970).
Scott et al, Chem. Abst., 69, 26735t (1968).

Primary Examiner—Paul M. Coughlan, Jr.
Assistant Examiner—D. B. Springer
Attorney, Agent, or Firm—Irving N. Feit

[57] ABSTRACT

The invention relates to a novel and technically advanced process for producing 5-cyano-5H-dibenz[b,f]azepine by reacting 5H-dibenz[b,f]azepine with a halocyanogen in the presence of strongly polar substances. 5-Cyano-5H-dibenz[b,f]azepine can be used as starting material for producing 5-carbamyl-10(11)-oxo-10,11-dihydro-5H-dibenz[b,f]azepine, which is known to have central-depressant, anticonvulsive and central-muscle-relaxing activity.

4 Claims, No Drawings

PROCESS FOR THE PRODUCTION OF 5-CYANO-AND 5-CARBOXAMIDO-5H-DIBENZ[B,F]AZEPINES

This is a continuation of application Ser. No. 198,887 filed on Oct. 20, 1980, now abandoned.

The invention relates to a novel and technically advanced process for producing 5-cyano-5H-dibenz[b,f]azepine by reacting 5H-dibenz[b,f]azepine with a halocyanogen in the presence of strongly polar substances. Halocyanogen denotes in this case cyanogen iodide, particularly however cyanogen chloride or cyanogen bromide.

5-Cyano-5H-dibenz[b,f]azepine can be used as starting material for producing 5-carbamyl-10(11)-oxo-10,11-dihydro-5H-dibenz[b,f]azepine, which is known to have central depressant, anticonvulsive and central-muscle-relaxing activity, by nitrating this starting material for example to give 5-cyano-10(11)nitro-5H-dibenz[b,f]azepine, hydrolysing in this the 5-cyano group to the 5-carbamyl group, subsequently reducing the 10(11)-nitro group down to the oximino stage, and hydrolysing this intermediate to obtain 5-carbamyl-10(11)-oxo-10,11-dihydro-5H-dibenz[b,f]azepine.

According to Tetrahedron Letters, 1973, pp. 2121-2124, 5-cyano-5H-dibenz[b,f]azepine can be obtained from 5-carboxamido-5H-dibenz[b,f]azepine by the splitting off of water by means of a mixture of triethylbenzylammonium chloride, chloroform and 50% aqueous sodium hydroxide solution. The disadvantage of this process is that the required starting material usually has to be firstly produced by reaction of 5H-dibenz[b,f]azepine with phosgene and subsequent reaction of the resulting carbonyl chloride with ammonia. A favourable process for producing substituted cyanamides is known from Houben-Weyl, Vol. VIII, p. 173, which process comprises reacting halocyanogen with an amine. The reaction is performed at low temperature in order to prevent the formation of guanidines. The formed hydrohalic acid has to be neutralised either by a calculated excess of amine or by the addition of alkali.- There is thus described for example the reaction of N-cyclohexyl-N-methylamine, as secondary amine in excess, with cyanogen chloride in benzene, at a temperature of 0°-5° C., to give N-cyclohexyl-N-methylcyanamide.

The application of such reaction conditions to the reaction of 5H-dibenz[b,f]azepine with for example cyanogen chloride did not however yield 5-cyano-5H-dibenz[b,f]azepine, so that a solution of the problem of producing 5-cyano-5H-dibenz[b,f]azepine from 5H-dibenz[b,f]azepine and a halocyanogen by methods analogous to known methods was not possible.

It has now been found that, surprisingly, the reaction according to the invention can be performed in the presence of strongly polar substances, by which means the disadvantages of having to operate in the presence of excess amine or additional alkali, and furthermore at a lower temperature, are avoided.

By virtue of their physical-chemical properties, such strongly polar substances can simultaneously serve as solvents, to which can optionally be added an additional solvent of nonpolar character. The quantity ratios of strongly polar substance to additional nonpolar solvent vary within wide limits, in that it is possible to use one strongly polar substance, or a mixture of such substances, on the one hand on its own as the sole solvent, or on the other hand in admixture with a nonpolar solvent up to catalytically effective amounts. The reaction temperature is within the range of 20°-100° C., preferably 50°-80° C.

Strongly polar compounds are for example aliphatic N-lower-alkyl- or N,N-di-lower-alkylamides of carboxylic acids of the formula R—COOH (I), wherein lower alkyl can in each case be substituted by lower alkoxy, and lower alkyl or lower alkoxy each contain up to 7 carbon atoms, particularly up to 4 carbon atoms, and R is lower alkyl having up to 5 carbon atoms, especially up to 3 carbon atoms.

Accordingly, aliphatic N-lower-alkyl- or N-lower-alkoxy-lower-alkylamides of lower-alkanecarboxylic acids are for example: N-methylacetamide, N-methylpropionamide, N-methoxymethylacetamide or N-methoxymethylpropionamide; whilst N,N-di-lower-alkyl-, N-lower-alkyl-N-lower-alkoxy-lower-alkyl- or N,N-di-lower-alkoxy-lower-alkylamides of lower-alkanecarboxylic acids are for example: N,N-dimethylacetamide, N,N-dimethylpropionamide, N-methyl-N-methoxymethylacetamide, N-methyl-N-methoxymethylpropionamide, N,N-di-(methoxymethyl)-acetamide or N,N-di-(methoxymethyl)-propionamide. Further strongly polar substances are derived from N-lower-alkylphosphoric acid amides, wherein lower alkyl has up to 4 carbon atoms, and are in particular hexamethyl- or hexaethylphosphoric acid triamide.

Strongly polar compounds are also optionally N-lower-alkylated cyclic carboxylic acid imides having for example 5-7 ring members, wherein lower alkyl has up to 4 carbon atoms, such as an optionally N-lower-alkylated, for instance, N-methylated, 2-oxo-alkyleneimine, for example pyrrolidone-(2), N-methylpyrrolidone-(2), piperidone-(2), N-methylpiperidone-(2), ε-caprolactam or N-methyl-ε-caprolactam.

Mentioned as further strongly polar substances are, inter alia: poly-lower-alkylated urea, such as tetra-lower-alkylurea, wherein lower alkyl has up to 3 carbon atoms, for example tetramethylurea, or sulfolane, also quaternary ammonium compounds, for example mono-, di-, tri- or tetraalkylammonium compounds, wherein each of the alkyl groups can have up to 18 carbon atoms, and can be substituted by an aryl group, such as phenyl which is unsubstituted or substituted for example by lower alkyl or lower alkoxy each having up to 7 carbon atoms, preferably up to 4 carbon atoms, or by halogen, hydroxyl or nitro, or salts thereof, for example with mineral acids, for instance sulfuric acid or hydrochloric acid.

Alkyl groups therefore of the type mentioned are for example: methyl, ethyl, propyl, isopropyl, n-butyl, n-pentyl, n-hexyl, n-decyl, lauryl, palmityl, stearyl or oleyl. Quaternary ammonium compounds of the stated type and salts thereof are for example: hydroxides of stearyl-trimethylammonium, oleyl-triethylammonium, lauryl-benzyldiethylammonium, palmityl-benzyl-dimethylammonium, benzyltrimethylammonium, benzyltriethylammonium, dibenzyl-diethylammonium, tribenzyl-n-propylammonium or tetrabenzylammonium, or salts thereof, for example with mineral acids, for instance hydrohalic acids, for example hydrochloric or hydrobromic acid or sulfuric acid, or organic acids, for example acetic acid. Strongly polar substances, for instance of the type mentioned, can also be used as mixtures.

Nonpolar liquids as further solvents are for example: halogenated lower alkanes, for instance chlorinated lower alkanes, for example chloroform, carbon tetrachloride, 1,2-dichloroethane or 1,1,1-trichloroethane; also solvents of aromatic character, for example optionally lower-alkylated or halogenated benzene, such as methylated or chlorinated benzene, for example benzene, toluene, xylene or chlorobenzene.

The invention relates in the first place to the above process for producing 5-cyano-5H-dibenz[b,f]azepine, wherein the halocyanogen used is cyanogen chloride or cyanogen bromide, and the strongly polar substances used are N,N-di-lower-alkylamides of carboxylic acids of the formula (I), in which lower alkyl in each case has up to 3 carbon atoms, and R has up to 2 carbon atoms, for example N,N-dimethylacetamide, N,N-diethylacetamide, N,N-di-n-propylacetamide, N,N-dimethylpropionamide or N,N-diethylpropionamide, also hexamethylphosphoric acid triamide, N-methylpyrrolidone-(2) or sulfolane, or the quaternary ammonium compound used is for example benzyltriethylammonium chloride or dibenzyl-diethylammonium chloride, and the nonpolar additional solvents optionally used are 1,2-dichloroethane or 1,1,1-trichloroethane, or the aromatic solvents used are benzene or toluene.

The invention relates to the above process for producing 5-cyano-5H-dibenz[b,f]azepine, wherein the halocyanogen used is cyanogen chloride, and the strongly polar substances used are for example N,N-dimethylacetamide or N,N-diethylacetamide, also hexamethylphosphoric acid triamide or sulfolane, or, as a quaternary ammonium compound, for example benzyltriethylammonium chloride, and the nonpolar additional solvents optionally used are 1,2-dichloroethane, 1,1,1-trichloroethane or toluene.

The invention relates in particular to the process described in the Examples.

The invention relates also to a novel and technically advanced process for producing 5H-dibenz[b,f]azepine-5-carboxamide by reacting 5H-dibenz[b,f]azepine with a halocyanogen, in the presence of strongly polar substances, to give 5-cyano-5H-dibenz[b,f]azepine, and subsequently hydrolysing this to obtain 5H-dibenz[b,f]azepine-5-carboxamide.

The 5-cyano-5H-dibenz[b,f]azepine required for this is produced by the process described above. This step is followed according to the invention by the conversion of the 5-cyano group in the 5-cyano-5H-dibenz[b,f]azepine into the 5-carboxamide group by means of hydrolysis. This can be performed with the aid of basic or acidic agents. Suitable basic agents for this purpose are for instance the oxides or hydroxides of alkaline-earth metals or alkali metals, for example magnesium or calcium hydroxide, also for example sodium hydroxide, optionally in the presence of a peroxide, such as hydrogen peroxide, or an alkali metal bicarbonate, such as sodium bicarbonate, in admixture with hydrogen peroxide, whilst acidic agents are for example mineral acids, such as sulfuric acid or polyphosphoric acid, also lower-alkane- or halogeno-lower-alkanecarboxylic acids having up to 4 carbon atoms, for example formic or acetic acid or trichloro- or trifluoroacetic acid, in admixture with mineral acids, for example sulfuric acid. Acidic agents are also Lewis acids, for example boron trifluoride, which can be in the form of a solution in a lower-alkanecarboxylic acid of the type described above, such as acetic acid, or in the form of a defined compound, for example of the formula $BF_3.2CH_3COOH$. A further solvent, for example a solvent of aromatic character, such as chlorobenzene, is optionally added to the reaction mixture. The reaction temperatures are within the range of $-5°$ to $+80°$ C., preferably $0°-40°$ C.

There is known from the German Patent Specification No. 1,136,707 a process for producing 5H-dibenz[b,f]azepine-5-carboxamide by reaction of 5H-dibenz[b,f]azepine with phosgene to give 5-chlorocarbonyl-5H-dibenz[b,f]azepine and the subsequent reaction thereof with ammonia to obtain the stated compound. The reaction of 5H-dibenz[b,f]azepine with phosgene is performed in toluene firstly at 70° C., and then under reflux. The subsequent reaction of this compound with ammonia is carried out in ethanol at boiling temperature.

Compared with this process, the process according to the invention has on the one hand the advantage of the above-described technically advanced method of producing 5-cyano-5H-dibenz[b,f]azepine required as an intermediate, and on the other hand the advantage that for the hydrolysis of the 5-cyano group to the 5-carboxamide group there are applied mild reaction conditions, which have a favourable effect particularly on the purity of the final product obtained. This is especially evident in the case where hydrolysis is performed by means of boron trifluoride, for example in the form of the defined complex with 2 mols of acetic acid, in that with the hydrolysis performed at normal temperature there can be isolated a novel crystalline addition compound of the hydrolysis product with boron trifluoride, which has not been described hitherto in the literature, and which can be converted by a subsequent treatment with water into the final product.

The Examples which follow serve to further illustrate the invention. The temperature values are given in degrees Centigrade.

EXAMPLE 1

97.0 g of 5H-dibenz[b,f]azepine are suspended in 320 ml of 1,2-dichloroethane, and after the addition of 18 ml of hexamethylphosphoric acid triamide the mixture is heated to 70°. There are fed in at this temperature 36.8 g of cyanogen chloride at a rate which just ensures that no escape of gas is observed at the head of a reflux condenser cooled to $-20°$. The clear light-brown solution formed is held for a further 15 hours at 70°; it is then cooled and is subsequently stirred up for one hour with 180 ml of water. After separation of the phases, the organic solution is vigorously shaken with 100 ml of 10% sodium hydroxide solution; it is then separated, and washed neutral with water. After drying over sodium sulfate and concentration by evaporation, there remains a dark-green crystalline residue, which is taken up in 150 ml of isopropanol, triturated, and filtered off with suction. Washing is performed twice with 50 ml of isopropanol each time to obtain greenish-white crystals which, according to the IR spectrum, are identical to authentic 5-cyano-5H-dibenz[b,f]azepine; m.p. 103°–107.5°; yield 100.0 g (91.7% of theory).

An analogously prepared mixture in 1,1,1-trichloroethane and hexamethyl-phosphoric acid triamide as solvent requires a total of 48 hours reaction time and a cyanogen chloride addition increased to 37.8 g; yield 105.0 g (96.3% of theory); m.p. 105.5°–107.1°.

EXAMPLE 2

97.0 g of 5H-dibenz[b,f]azepine are suspended in 320 ml of 1,2-dichloroethane, and after the addition of 4 ml of hexamethyl-phosphoric acid triamide the mixture is heated to 60°. A reflux condenser cooled to $-20°$ is mounted, and 50 g of cyanogen chloride are introduced in the course of 3 hours. The temperature is held at 60° for a further 10 hours with stirring, a clear solution being obtained after 5 hours. The reflux condenser is replaced by a descending condenser, and by applying a slight vacuum at the same temperature, 350 ml of a mixture of cyanogen chloride and 1,2-dichloroethane are distilled off into a cooled receiver. In order to remove unreacted cyanogen chloride, the proportion of 1,2-dichloroethane distilled off is continuously replenished by the addition of fresh 1,2-dichloroethane into the distillation flask. The distillate is either used for a further charge, or freed from cyanogen chloride by treatment with aqueous sodium hydroxide solution and processed in the customary manner. To the contents of the distilling flask are added 200 ml of water; the mixture is then cooled to room temperature, and rendered permanently alkaline by the dropwise addition of 30% sodium hydroxide solution. After phase separation, the organic phase is filtered, washed twice with water and concentrated in vacuo. The residue is taken up in methanol and yields, after one hour's cooling in an ice-bath, 95.7 g of 5-cyano-5H-dibenz[b,f]azepine, which, according to the IR spectrum, is identical to authentic material; m.p. 108°–109°. A second crystallisation of 2.5 g can be obtained from the mother liquor; total yield =98.2 g (90% of theory).

EXAMPLE 3

97.0 g of 5H-dibenz[b,f]azepine are dissolved in 320 ml of N,N-dimethylacetamide, and, by a procedure analogous to that of Example 1, 40.0 g of cyanogen chloride are fed in at 30° in the course of 110 minutes. The temperature is raised during 120 minutes to 68° and is held there for three hours. After cooling, there are added 200 ml of 10% sodium hydroxide solution and 500 ml of water; the supernatant aqueous phase is decanted, and the semicrystalline product obtained is subsequently washed twice with 500 ml of water each time. The residue is taken up in methylene chloride; the solution is washed neutral with water and, after concentration by evaporation, taken up in isopropanol, whereupon 5-cyano-5H-dibenz[b,f]azepine is obtained; m.p. 108.3°–108.7°; yield: 76.8 g (70% of theory).

EXAMPLE 4

By a procedure analogous to that described in Example 1, 97.0 g of 5H-dibenz[b,f]azepine are suspended in 320 ml of 1,2-dichloroethane, and 2 ml of N,N-dimethylacetamide are added. The temperature is raised to 60°, and 50 g of cyanogen chloride are introduced in the course of 2 hours, the reflux condenser being cooled to $-17°$ in order to avoid loss of cyanogen chloride. The mixture is kept at 60° for 16 hours; a descending condenser is then fitted, and at normal pressure 200 ml of a mixture of cyanogen chloride and 1,2-dichloroethane are distilled off into a cooled receiver. During distillation, the 1,2-dichloroethane passing over is continuously replaced by fresh solvent in order to remove residual cyanogen chloride. The contents of the flask are cooled to room temperature; 200 ml of water are added, and the mixture is rendered permanently alkaline by the addition of 30% sodium hydroxide solution. Further processing, analogous to that in Example 2, yields 96.3 g of 5-cyano-5H-dibenz[b,f]azepine, which, according to the IR spectrum, is identical to authentic material; m.p. 108°–109°. A further 4 g of final product can be obtained from the mother liquor, and the total yield is 100.3 g (92% of theory).

EXAMPLE 5

6 g of cyanogen chloride are introduced within 1 hour into a solution, heated to 80°, of 9.64 g of 5H-dibenz[b,f]azepine and 1 g of benzyltriethylammonium chloride in 40 ml of toluene. The reaction mixture is stirred for a further 5 hours at 80°; it is then cooled to room temperature and washed with 40 ml of 2 N sodium hydroxide solution; the organic phase is separated, and is then evaporated to dryness in vacuo to obtain 5-cyano-5H-dibenz[b,f]azepine, which is identical to the product obtainable according to Example 1; m.p. 107°–108°; yield 6.2 g (56.9% of theory).

EXAMPLE 6

6.0 g (0.027 mol) of 5-cyano-5H-dibenz[b,f]azepine are dissolved in a mixture of 80 ml of acetic anhydride and 20 ml of acetic acid. The temperature is raised to 50°, and in the course of 1½ hours there is added dropwise the solution of 5.6 g (0.08 mol) of sodium nitrite in 10 ml of water, during which time the temperature is not allowed to exceed 55°. The temperature is held at 50° for a further 2 hours, and the solvent is then distilled off at reduced pressure and a bath temperature of 50°. The residue is digested twice with 100 ml of ice-water each time, and subsequently taken up in 80 ml of ethanol. After a standing time of several hours at 0°, the yellow crystals which have precipitated are filtered off with suction, and washed with a small amount of ethanol. The 5-cyano-10-(11)-nitro-5H-dibenz[b,f]azepine obtained melts at 175°–176° with decomposition; yield 5.2 g (72% of theory).

The analytical and spectroscopic data are in agreement with the assumed structure.

EXAMPLE 7

50 ml of a solution of 15 percent by weight of BF$_3$ in acetic acid (0.11 mol) are added at room temperature to a suspension of 26.3 g (0.1 mol) of 5-cyano-10(11)-nitro-5H-dibenz[b,f]azepine in 100 ml of acetic acid. The temperature slowly rises to 34° with the complete dissolving of the starting material. There are added at 30° in the course of 5 minutes 30 ml of water, which leads to a renewed temperature rise to 37°. At this temperature, 40 g of iron powder are added portionwise in the course of 20 minutes, during which time the temperature is held at 65°–70° by occasional cooling. After the exothermic reaction has subsided, the mixture is stirred for a further 15 minutes, and subsequently the inorganic material is filtered off, and is afterwards washed three times with a small amount of acetic acid. The whole filtrate is added dropwise, with thorough stirring, to 1½ liters of water, the formed precipitate is filtered off after 2 hours' stirring, and washed neutral with water. There is thus obtained after drying at 60° in vacuo 5-carbamyl-10(11)-oxo-10,11-dihydro-5H-dibenz[b,f]azepine, which according to the IR spectrum is identical to authentic material; yield 23.0 g (91.2% of theory).

EXAMPLE 8

The solution of 7.7 ml of the complex BF$_3$.2CH$_3$COOH in 19 ml of acetic acid is added to one portion to a suspension of 10.5 g (0.05 mol) of 5-cyano-5H-dibenz[b,f]azepine in 100 ml of chlorobenzene. With a slight temperature rise there is formed a clear light-green solution, from which after 5 minutes a crystalline addition compound of 5H-dibenz[b,f]azepine-5-carboxamide with BF₃ crystallises out. Stirring is performed for one hour in an ice-bath; the product is then filtered off, and washed with chlorobenzene and petroleum ether. The crystalline material is suspended in 150 ml of water, stirred for one hour at room temperature, filtered off, and washed neutral with water. The yield after drying at 50° in vacuo is 11.3 g (95.7% of theory) of crude 5H-dibenz[b,f]azepine-5-carboxamide, which is recrystallised from ethanol/water, and is shown by means of DC and IR analysis to be identical to authentic material.

EXAMPLE 9

2.0 g of 5-cyano-5H-dibenz[b,f]azepine are suspended in 40 ml of methanol, and 10 ml of 30% $H_2O_2$ are added at room temperature. The mixture is stirred for 30 minutes, and 10 g of sodium hydrogen carbonate are then added portionwise. After being stirred overnight at room temperature, the mixture is diluted with 50 ml of water; the formed precipitate is subsequently filtered off, and washed several times with water. The yield after drying is 3.0 g (95.2% of theory) of 5H-dibenz[b,f]azepine-5-carboxamide, which is shown by means of DC and IR analysis to be identical to authentic material.

EXAMPLE 10

2.0 g of 5-cyano-5H-dibenz[b,f]azepine are introduced portionwise at room temperature into a mixture of 16 ml of acetic acid and 4 ml of concentrated sulfuric acid, and a complete solution is obtained after one hour's stirring. It is poured into 200 ml of ice-water, and the formed white suspension is stirred for 10 minutes; filtration is then performed and the precipitate is washed neutral with water. The yield is 2.0 g (95.2% of theory) of 5H-dibenz[b,f]azepine-5-carboxamide, which according to DC and IR analysis is identical to authentic material.

What is claimed is:

1. A process for producing 5-cyano-5H-dibenz[b,f]azepine comprising reacting 5H-dibenz[b,f]azepine with cyanogen chloride or cyanogen bromide in the presence of at least catalytically effective amounts of N,N-dimethylacetamide, N,N-diethylacetamide, N,N-di-npropylacetamide, N,N-dimethylpropionamide or N,N-diethylpropionamide, hexamethylphosphoric acid triamide, N-methyl-pyrrolidone-(2), sulfolane, benzyltriethylammonium chloride or dibenzyl-diethylammonium chloride as strong polar substances within the temperature range of 20°–100° C.

2. A process for producing 5H-dibenz[b,f]azepine-5-carboxamide comprising reacting 5H-dibenz[b,f]azepine with cyanogen chloride or cyanogen bromide in the presence of at least catalytically effective amount of N,N-dimethylacetamide, N,N-diethylacetamide, N,N-di-n-propylacetamide, N,N-dimethylpropionamide or N,N-diethylpropionamide, hexamethylphosphoric acid triamide, N-methyl-pyrrolidone-(2), sulfolane benzyltriethylammonium chloride or dibenzyl-diethylammoniumchloride as strong polar substances within the temperature range of 20°–100° C., hydrolysing the 5-cyano-5H-dibenz[b,f]azepine obtained by treating with formic or acetic acid or trichloro- or trifluoroacetic acid in admixture with sulfuric acid and finally treating the mixture with water at a temperature range of −5° to +80° C.

3. A process for producing 5H-dibenz[b,f]azepine-5-carboxamide comprising reacting 5H-dibenz[b,f]azepine with cyanogen chloride or cyanogen bromide in the presence of at least catalytically effective amounts of N,N-dimethylacetamide, N,N-diethylacetamide, N,N-di-n-propylacetamide, N,N-dimethylpropionamide or N,N-diethylpropionamide, hexamethylphosphonic acid triamide, N-methyl-pyrrolidone-(2), sulfolane, benzyltriethylammonium chloride or di-benzyl-diethylammonium chloride as strong polar substances within the temperature range of 20°–100° C., hydrolysing the 5-cyano-5H-dibenz[b,f]azepine obtained by reacting with 30% $H_2O_2$ and sodium hydrogen carbonate and finally treating the mixture with water at a temperature range of −5° to +80° C.

4. A process for producing 5H-dibenz[b,f]azepine-5-carboxamide comprising reacting 5H-dibenz[b,f]azepine with cyanogen chloride or cyanogen bromide in the presence of at least catalytically effective amounts of N,N-dimethylacetamide, N,N-diethylacetamide, N,N-di-n-propylacetamide, N,N-dimethylpropionamide or N,N-diethylpropionamide, hexamethylphosphoric acid triamide, N-methyl-pyrrolidone-(2), sulfolane, benzyltriethylammonium chloride or dibenzyl-diethylammonium chloride as strong polar substances within the temperature range of 20°–100° C., hydrolyzing the 5-cyano-5H-dibenz[b,f]azepine obtained by reacting with the complex $BF_3.2CH_3COOH$ in acetic acid and chlorobenzene and then decomposing the crystalline addition compound of 5H-dibenz[b,f]azepine 5-carboxamide with BF₃ obtained by treatment with water in a temperature range of −5° to +80° C.

* * * * *